(12) United States Patent
Katscher et al.

(10) Patent No.: US 11,373,304 B2
(45) Date of Patent: Jun. 28, 2022

(54) MEDICAL ANALYSIS METHOD FOR PREDICTING METASTASES IN A TEST TISSUE SAMPLE

(71) Applicant: KONINKLIJKE PHILIPS N.V., Eindhoven (NL)

(72) Inventors: Ulrich Katscher, Norderstedt (DE); Karsten Sommer, Hamburg (DE); Axel Saalbach, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 3 days.

(21) Appl. No.: 16/962,545

(22) PCT Filed: Jan. 17, 2019

(86) PCT No.: PCT/EP2019/051087
§ 371 (c)(1),
(2) Date: Jul. 16, 2020

(87) PCT Pub. No.: WO2019/141748
PCT Pub. Date: Jul. 25, 2019

(65) Prior Publication Data
US 2020/0410672 A1   Dec. 31, 2020

(30) Foreign Application Priority Data

Jan. 18, 2018   (EP) ..................................... 18152265

(51) Int. Cl.
*G06K 9/00* (2022.01)
*G06T 7/00* (2017.01)
(Continued)

(52) U.S. Cl.
CPC .......... *G06T 7/0012* (2013.01); *G06V 20/698* (2022.01); *G16H 10/60* (2018.01);
(Continued)

(58) Field of Classification Search
CPC ......... G06T 7/0012; G06T 2207/10081; G06T 2207/10088; G06T 2207/10104;
(Continued)

(56) References Cited

U.S. PATENT DOCUMENTS

| 8,855,387 | B2 * | 10/2014 | Hamadeh | .................. G06T 7/11 |
| | | | | 382/128 |
| 2012/0010528 | A1 * | 1/2012 | Donovan | ............. G06V 20/698 |
| | | | | 382/128 |

(Continued)

FOREIGN PATENT DOCUMENTS

WO    2009084995 A1    7/2009

OTHER PUBLICATIONS

Freiman Moti et al "Classification of Suspected Liver Metastases Using FMRI Images . . . " ECCV 2016 Conference p. 93 (Sep. 6, 2008).

(Continued)

*Primary Examiner* — Van D Huynh

(57) ABSTRACT

The present disclosure relates to a computer implemented medical analysis method for predicting metastases (300) in a test tissue sample, the method comprising: providing a first machine learning model (154) having an input and an output, receiving a description (401) of a tumor (304) and first image data (148) of a test tissue sample of an anatomy region (306), the test tissue sample being free of metastases (300), providing the first image data (148) and the tumor description (401) to the input of the first machine learning model (154), in response to the providing, receiving from the output of the first machine learning model (154) a prediction of occurrence of metastases (300) originating from the tumor (304) in the test tissue sample, and providing the prediction.

14 Claims, 4 Drawing Sheets

(51) Int. Cl.
*G16H 10/60* (2018.01)
*G06V 20/69* (2022.01)

(52) U.S. Cl.
CPC .............. *G06T 2207/10081* (2013.01); *G06T 2207/10088* (2013.01); *G06T 2207/10104* (2013.01); *G06T 2207/20076* (2013.01); *G06T 2207/20081* (2013.01); *G06T 2207/20084* (2013.01); *G06T 2207/30096* (2013.01); *G06V 2201/03* (2022.01)

(58) Field of Classification Search
CPC . G06T 2207/20076; G06T 2207/20081; G06T 2207/20084; G06T 2207/30096; G06T 2207/10072; G16H 10/60; G06K 9/00147; G06K 2209/05
USPC .......................................................... 382/128
See application file for complete search history.

(56) References Cited

U.S. PATENT DOCUMENTS

| | | | | |
|---|---|---|---|---|
| 2012/0329672 | A1* | 12/2012 | Croce | C12Q 1/6886 506/9 |
| 2013/0094704 | A1* | 4/2013 | Hamadeh | G06N 3/02 382/103 |
| 2013/0224192 | A1* | 8/2013 | Lidereau | C12Q 1/6886 435/7.1 |
| 2017/0084021 | A1* | 3/2017 | Athelogou | G06T 7/0012 |
| 2017/0193175 | A1* | 7/2017 | Madabhushi | G06V 10/454 |
| 2017/0299570 | A1* | 10/2017 | Loparic | G01N 33/4833 |
| 2018/0232883 | A1* | 8/2018 | Sethi | G06K 9/6267 |
| 2019/0113423 | A1* | 4/2019 | Goodman | G01N 33/4833 |

OTHER PUBLICATIONS

International Search Report and Written Opinion from PCT/EP2019/051087 dated Feb. 20, 2019.
BZ Ring et al. "Predicting the sites of metastases" Genome Biology 2005, 6:241.
Auperin A, et al. "Prophylactic cranial irradiation for patients with small-cell lung cancer in complete remission" N Engl J Med 1999, 341:476.
Alex Krizhevsky et al. "Imagenet classification with deep convolutional neural networks," Advances in Neural Information Processing Systems,2012.
J. Redmon, et al. "You Only Look Once: Unified, Real-Time Object Detection," 2016 IEEE Conference on Computer Vision and Pattern Recognition (CVPR), Las Vegas, NV, 2016, pp. 779-788, doi: 10.1109/CVPR.2016.91.
Noh, H., et al. "Learning deconvolution network for semantic segmentation" In Proceedings of the IEEE International Conference on Computer Vision, 1520-1528, 2015.
Olaf Ronneberger et al. "U-Net: Convolutional Networks for Biomedical Image Segmentation" Medical Image Computing and Computer-Assisted Intervention (MICCAI), Springer, LNCS, vol. 9351: 234-241, 2015.
Koizumi et al "Diagnostic Performance of a Computer Assisted Diagnosis System for Bone Scintigraphy of Newly Developed Skeletal Metastasis . . . " Ann Nucl Med (2017) 31 p. 521-528.
Roth et al. "Detection of Sclerotic Spine Metastases Via Random Aggregation of Deep Convulutional Neural Network Classifications" Computational Methods and Clinical Applications for Spine Imaging workshop MICCAI 2014.
Litjens et al. "A Survey on Deep Learning in Medical Image Analysis" Medical Image Analysis 42 (2017) p. 60-88.

* cited by examiner

MEDICAL ANALYSIS METHOD FOR PREDICTING METASTASES IN A TEST TISSUE SAMPLE

CROSS REFERENCE TO RELATED APPLICATIONS

This application is a U.S. national phase application of International Application No. PCT/EP2019/051087 filed on Jan. 17, 2019, which claims the benefit of EP Application Serial No. 18152265.7 filed on Jan. 18, 2018 and is incorporated herein by reference.

FIELD OF THE INVENTION

The invention relates to a medical analysis method for predicting metastases in a test tissue sample, a medical analysis system for predicting metastases in a test tissue sample, a MRI system and a computer program product.

BACKGROUND OF THE INVENTION

Many tumor types tend to spread across the body via metastases. Clinicians are looking for ways to determine as early as possible the location of potential metastases once a primary tumor is detected. A correct determination of a metastasis location offers therapeutic advantages. For example, prophylactic irradiation reduces the incidence of metastases and improves overall survival.

Various imaging technologies are known in art in order to image tissue of a subject. Examples are magnetic resonance imaging (MRI), computer tomography (CT), ultrasound imaging (US) and positron emission tomography imaging.

Magnetic resonance imaging (MRI) is state of the art imaging technology which allows cross-sectional viewing of objects like the human body with unprecedented tissue contrast. MRI is based on the principles of nuclear magnetic resonance, a spectroscopic technique used by scientists to obtain microscopic chemical and physical information about molecules. The basis of both, nuclear magnetic resonance and MRI is the fact, that atomic nuclei with non-zero spin have a magnetic moment. In medical imaging, for example nuclei of hydrogen atoms are studied since they are present in the body in high concentrations like for example water. The nuclear spin of elementary particles can resonate at a resonant frequency, if a strong DC magnetic field is applied. This magnet resonance (MR) frequency is determined by the level of magnetic flux of the DC magnetic field. In the MRI scanner, the magnetic field matches the selected resonance frequency only at a position in space. Only at this position the presence of these particles can be detected. By varying this position, an image can be measured.

The needed strong DC magnetic field (BO field) is typically generated by superconducting magnets. In order to vary this field, such that it matches a given radio-frequency only at one position, a field gradient is generated using gradient coils. A field gradient can vary over time to achieve a scan.

To excite nuclear resonances, the RF coil generates a high frequency magnetic field at the nuclear resonance. The magnetic field must direct in a radial direction with respect to the axis of the MRI scanner. To achieve a radial magnetic field in all directions, a rotating field is used, which points in any radial direction at one point of time during one period. This is achieved using for example a so called 'birdcage' arrangement. Currents in opposing slabs of the birdcage flow in opposite direction and thus generate a radial field. Currents in neighbor slabs have a phase shift, such that the field rotates.

The coil is generally a highly resonant antenna, designed for generating the well-defined magnetic field inside the human body.

WO2009/084995 A1 relates to a detection system for automatic detection of bone cancer metastases from a set of isotope bone scan images of a patients skeleton, the system comprising a shape identifier unit, a hotspot detection unit, a hotspot feature extraction unit, a first artificial neural network unit, a patient feature extraction unit, and a second artificial neural network unit.

The US-patent application US2017/0193175 discloses a computational method of predicting recurrence of non-small cell lung cancer (NSCLC) from a digitised stained histopathology image. An automatic deep learning provides the probability of recurrence in the (same) region of NSCLC. That is, from a biopsy of a small area of tissue, the liklelihood of cancer recurrence in the same organ from which the biopsy was taken is predicted.

SUMMARY OF THE INVENTION

Embodiments of the invention provide for a computer implemented medical analysis method for predicting metastases in a test tissue sample, the method comprising providing a first machine learning model having an input and an output, receiving a description of a tumor and first image data of a test tissue sample of an anatomy region, the test tissue sample being free of metastases, providing the first image data and the tumor description to the input of the first machine learning model, in response to the providing, receiving from the output of the first machine learning model a prediction of occurrence of metastases originating from the tumor in the test tissue sample, and providing the prediction.

The term 'image data' relates to data that can be transformed into an image and displayed on a user interface like a computer screen.

An 'anatomy region' is any predefined region of the anatomy of a subject, like for example a person or an animal. A region may comprise a certain organ like the liver or the brain, or it may comprise a certain area like the spine area, a knee, a shoulder etc.

The term "machine learning" refers to a computer algorithm used to extract useful information from training data sets by building probabilistic models (referred to as machine learning models) in an automated way. The machine learning may be performed using one or more learning algorithms such as such as classification and regression techniques (e.g. Support Vector methods, Trees, Neural Networks, . . . ). A "model" may for example be an equation or set of rules that makes it possible to predict an unmeasured value (e.g. which tag corresponds to a given token) from other, known values and/or to predict or select an action to maximize a future reward. According to one embodiment, the machine learning model is a deep learning model.

Embodiments of the invention may have the advantage that the development of metastases may be predicted before the metastases themselves are present in the anatomy region. For example, a certain tumor present in the subject may in future cause the development of metastases. The above described method aims at predicting this development including an optional prediction of the development over time. This may even allow for a precise prediction ("intra-organ") of metastases, i.e., a possible location within a specific organ.

Embodiments may thus suggest to apply machine learning for intra-organ prediction of metastasis locations: after detection of a primary tumor, the target organs which are most likely affected by metastases may for example be imaged with one or more suitable imaging modalities providing sufficient radiologic information. The resulting images enter a suitably trained machine learning algorithm, which yields information on the probability of intra-organ locations of expected metastases. That is, upon detection of a primary tumour in one organ or tissue region, then from the description of the detected primary tumour and the first image data of the test tissue sample of the anatomy region that is separate from the detected primary tumour and being (still) free of metastases, the first machine learning model is capable of predicting the occurrence of metastases (in due course) in said anatomic region. In particular, the first machine learning model may predict the occurrence of metastases in other, different parts of the patient's body, i.e. other organs or tissue regions than the organ or tissue region in which the primary tumour has been detected.

In accordance with an embodiment of the invention, the method further comprises receiving training sets for multiple different ones of training tissue samples of the anatomy region, each training set comprising for a respective one of the training tissue samples second image data and third image data, the third image data being data acquired after occurrence of metastases in the subject from which the training tissue sample originates, the second image data representing the training tissue sample free of metastases, wherein each training set further comprises a description of the tumor in the subject from which the training tissue sample originates, and executing a learning algorithm on the training sets for generating the first machine learning model. Thus, the second machine learning model may may using the third image data, predict the occurrence of metastases in other, different parts of the patient's body, i.e. other organs or tissue regions than the organ or tissue region in which the primary tumour has been detected This may have the benefit that even without prior knowledge on the exact processes leading to the development of metastases may still be possible to accurately provide for a machine learning model that is able to make the above described metastases prediction. By means of the training sets it may be possible to automatically attribute to certain anatomy regions a certain susceptibility for metastases development, which may even depend on a certain type of anatomical shaping of the anatomy regions that is visible in the second image data. For example, the machine learning model may therefore describe that a certain shaping of the brain with a certain convolution of the brain in a specific brain area is more susceptible to the development of metastases compared to a slightly different shaping of that brain area with a different convolution of the brain in that area.

It has to be noted that the third image data is data acquired after occurrence of metastases in the subject, wherein the metastases are not necessarily located in the anatomy region. Thus, in case the third image data does not have any metastases this will be an indication for the learning algorithm that tissue corresponding to said third image data is less susceptible to the formation of metastases. To the contrary, in case the third image data is representing the training tissue sample affected my metastases this will be an indication for the learning algorithm that tissue corresponding to said third image data is more susceptible to the formation of metastases. In any case, the second image data is always free of any metastases.

For example, the learning algorithm may comprise a deep learning network, which learns to predict the probability of a metastasis in a specific anatomical region by providing the second image data together with information about the appearance of metastasis in a follow-up acquisition.

In accordance with an embodiment, the second image data and the third image data represent a 3D volume of the anatomy. For example, the image data may be acquired using a 2D multislice acquisition or using a 3D acquisition in order to provide the 3D volume.

In accordance with an embodiment, the description of the tumor comprising anyone of: a spatial location of the tumor with respect to the anatomy of the subject carrying the tumor, a classification of the tumor, image data of the tumor. Depending on the location of a tumor the development of metastases may be differently. The classification of the tumor may be provided for example in accordance with the WHO/IARC or TNM classification of tumors, which is well known in the art. Tumor classification may thus be based on consensus of histopathological opinion, even with consideration of molecular pathology.

For example, the description of the tumor may comprise CT or MR or X-Ray image data. Based on the size, shape and location of the tumor the learning algorithm may be able to predict the probability of a metastasis in a specific anatomical region that is different from the region which comprises the tumor itself.

In accordance with an embodiment, the prediction of occurrence of metastases is comprising anyone of: an indication if the test tissue sample will be affected by metastases originating from the tumor; a probability map across the anatomy region having indications at which discrete locations of the anatomy region will be affected by metastases originating from the tumor.

Thus, depending on the available training sets the prediction may reach from a simple yes/no information if the test tissue sample will somewhere be affected by metastases originating from the tumor to a whole map which in detail provides information at which probability which spatial location within the tissue sample will be affected by metastases originating from the tumor.

For example, the indication is comprising anyone of: a probability value, the probability value describing the probability at which the metastases have to be expected; a binary value, the binary value describing if metastases have to be expected or not. The probability value may be given as a percentage (e.g. 100%, 50%, 25% . . . ) or as a binary value (e.g. '1'='yes, metastases probable', '0'='no metastases probable').

Thus, for each anatomy it may be possible to predict a probability or a binary description that a metastasis will occur. A region proposal may come with a location/spatial extend (and a score/binary decision). Finally, for a segmentation like approach every voxel or pixel may have a binary decision/probability score. In accordance with an embodiment, the first image data, the second image data, the third image date and the image data of the tumor are anyone of: magnetic resonance image data, computed tomography image data, ultrasound image data, positron emission tomography image data, X-Ray data. Thus, the method is free to use any image data available from the subject for which the metastases have to be predicted. The training sets may comprise for example a set of second and third image data from MRI and a set of second and third image data from CT. The reason is that both sets have images that show the anatomy region with different information content 'contrast'. In combination, the highest information content is provided.

The images acquired during training and prediction phase thus can be from a single or multiple imaging modalities, e.g. magnetic resonance (MR), computed tomography (CT), ultrasound (US), or positron emission tomography (PET). Furthermore, it can be advantageous to acquire with each modality multiple image sets with different contrasts, e.g., MR images with T1/T2/diffusion-weighting, pre- and post contrast agent injection, etc. A suitable trade-off between imaging effort and predictive power has to be found. Furthermore, the approach is not limited to imaging data only, but could incorporate information such as age, gender, lab values, or the patient history.

For that reason, in accordance with an embodiment, the method is further comprising receiving medical history data of the subject carrying the tumor and providing the medical history data to the input of the machine learning model, the training set further comprising medical history data of the subject carrying the tumor. For example, a heavy smoker may be more susceptible for the development of metastases in a certain region of anatomy like for example the lung compared to a non-smoking individual.

Generally, the medical history or anamnesis of a patient is information gained by a physician by asking specific questions, either of the patient or of other people who know the person and can give suitable information, with the aim of obtaining information useful in formulating a diagnosis and providing medical care to the patient. Examples of the medical history data are: identification and demographics like name, age, height, weight; past medical history including major illnesses, any previous surgery/operations; family diseases; regular and acute medications; allergies etc.

In accordance with an embodiment, the third image data is a set of timely resolved image data, wherein the indications are time resolved. This may have the benefit that a time resolved prediction of the development of metastases may be performed. For example, in case two locations for highly probable development of metastases are predicted, a respective prophylactic irradiation treatment could be first performed for the training tissue for which the development of metastases is to be expected first (based on the prediction) and after completeness of that irradiation treatment a further prophylactic irradiation treatment could be second performed for the training tissue for which the development of metastases is to be expected at a later point in time (based on the prediction). This may help to concentrate pre-treatment on the most important tissue areas avoiding to stress the subject with too many parallel pre-treatments that typically are performed parallel to a rather wearisome treatment of the main tumor (i.e. the metastases source).

In accordance with an embodiment, the method is further comprising analyzing the third image data for the presence of metastases in the respective training tissue sample, and annotating the third image data regarding the results of the analysis. For example, the analysis is performed using a second machine learning model. The second machine learning model is provided in order to automatically identify the metastases in the third image data of training sets of the training tissue samples of the anatomy region, whereas the first machine learning model is provided to predict the occurrence of metastases based on the first image data that is free of metastases.

In accordance with an embodiment, the learning algorithm being a deep learning algorithm. Preferably, the deep learning algorithm is a convolutional neural network (CNN). CNNs have been developed for image classification purposes, and demonstrated a superior performance in this domain. A CNN consists of a sequence of interconnected layers (i.e. convolutional layer, max-pooling layer, . . . ) resembling the feature extraction step in a classical image processing pipeline, followed by one or more fully connected layers. CNNs are usually trained to predict class labels or probabilities for natural images, or to provide diagnosis for medical images, but the underlying concept can be transferred directly to the described technique of metastases prediction. Even though CNNs have been developed primarily for the processing of image data, it should be noted that also non-image data like the description of the tumor and/or the medical history data of the subject could be integrated e.g. in terms of additional input connections at the level of the fully connected layers.

As a further example of deep learning algorithms, for the prediction of metastases location (including their probabilities), region proposal networks can be considered. Here, in contrast to conventional CNNs, the output neurons no longer correspond to discrete class labels but to voxel locations and metastases probabilities. For this purpose, it may be assumed that the images of the anatomy region are transformed in a normalized reference frame:

In accordance with an embodiment, the deep learning algorithm may thus be based on a convolutional neural network architecture, the method further comprising: transforming for all training sets the second image data and the third image data into a common reference image frame of the anatomy region; performing the executing of the learning algorithm on the training sets comprising the transformed image data for generating the first machine learning model. Of course, the first image data also should be transformed into the common reference image frame such that for all image data that is used for the training and prediction the algorithm and the model know which parts of the images correspond to each other.

Generally, deep learning-based techniques may be employed for the generation of probability maps. Given images of the primary tumor, in combination with an annotated metastases region in the target organ (the anatomy region), the probability at voxel level could be estimated using a patch-wise analysis of a corresponding CNN (centered at the voxel of interest). Alternatively, more efficient network structures from the field of semantic image segmentation could be employed, like fully convolutional networks.

In another aspect, the invention relates to a computer program product comprising machine executable instructions for execution by a processor, wherein execution of the machine executable instructions causes the processor to execute the method as described above.

In another aspect, the invention relates to a medial analysis system for predicting metastases in a test tissue sample, the system comprising a memory containing machine executable instructions and a processor for controlling the medical analysis system, wherein execution of the machine executable instructions causes the processor to: providing a first machine learning model having an input and an output; receiving a description of a tumor and first image data of a test tissue sample of an anatomy region, the test tissue sample being free of metastases; providing the first image data and the tumor description to the input of the first machine learning model; in response to the providing, receiving from the output of the first machine learning model a prediction of occurrence of metastases originating from the tumor in the test tissue sample; and providing the prediction.

In another aspect, the invention relates to an MRI system comprising the described medical analysis system, the MRI system being configured for acquiring the first image data.

It is understood that one or more of the aforementioned embodiments of the invention may be combined as long as the combined embodiments are not mutually exclusive.

As will be appreciated by one skilled in the art, examples discussed in this disclosure may be embodied as an apparatus, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage may be any volatile or non-volatile computer-readable storage medium.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects are described with reference to flow charts, block diagrams of methods, apparatus (systems) and computer program products. It is understood that each block or a portion of the blocks of the flowcharts, illustrations, and/or block diagrams, may be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) display, Electroluminescent display (ELD), Plasma display panel (PDP), Liquid crystal display (LCD), Organic light-emitting diode display (OLED), a projector, and Head-mounted display.

Magnetic Resonance (MR) data is defined herein as being the recorded measurements of radio frequency signals emitted by atomic spins using the antenna of a magnetic resonance apparatus during a magnetic resonance imaging scan. Magnetic resonance data is an example of medical imaging data. A Magnetic Resonance (MR) image is defined herein as being the reconstructed two or three dimensional visualization of anatomic data contained within the magnetic resonance imaging data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

In the following, like numbered elements in the figures are either similar elements or perform an equivalent function. Elements which have been discussed previously will not necessarily be discussed in later figures if the function is equivalent.

Various structures, systems and devices are schematically depicted in the figures for purposes of explanation only and so as to not obscure the present invention with details that are well known to those skilled in the art. Nevertheless, the attached figures are included to describe and explain illustrative examples of the disclosed subject matter.

Figure 1:
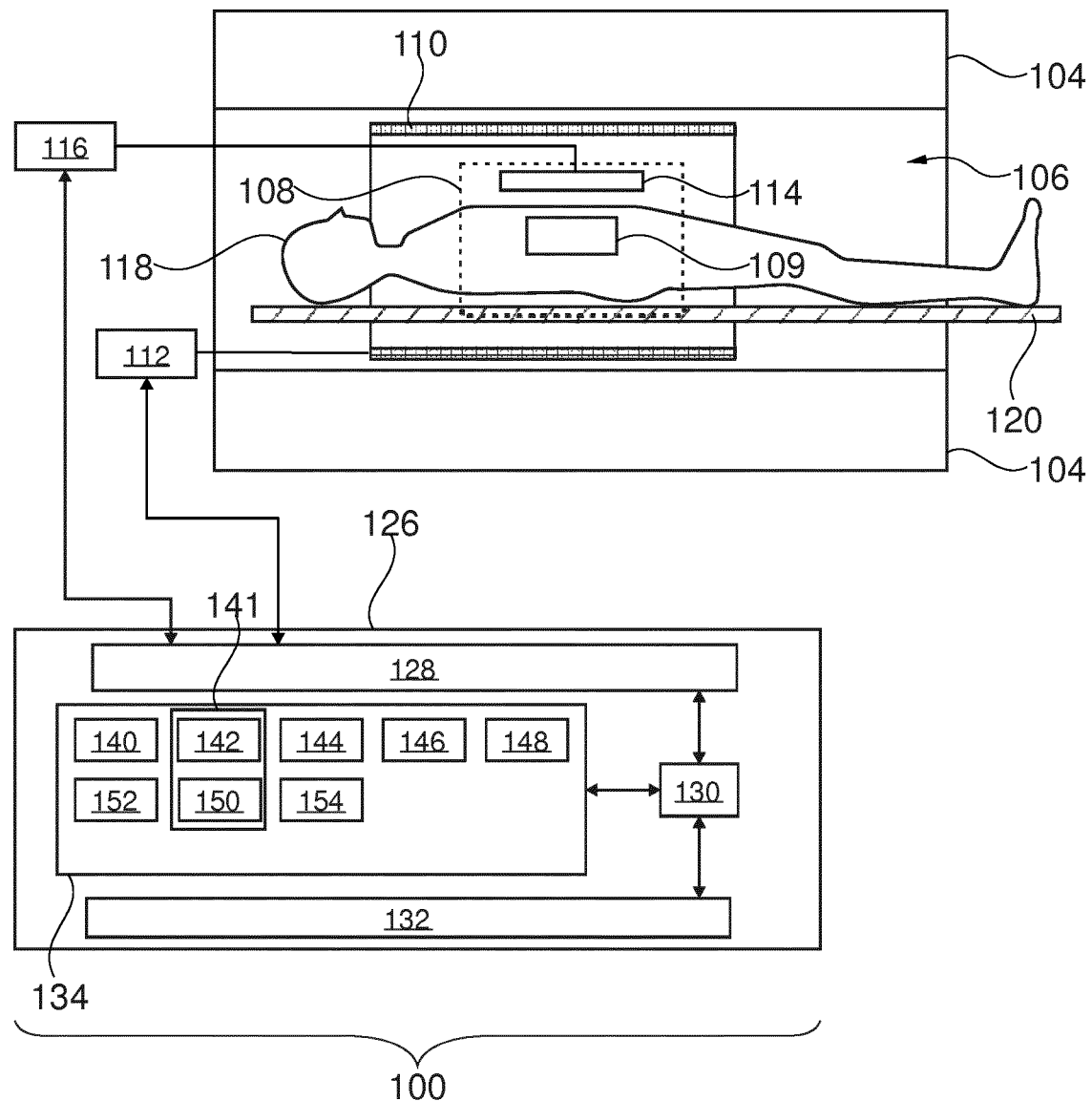
FIG. 1 illustrates an example of a magnetic resonance imaging system.

FIG. 1 shows an example of a magnetic resonance imaging system 100 with a magnet 104. The magnet 104 is a superconducting cylindrical type magnet with a bore 106 through it. The use of different types of magnets is also possible; for instance, it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging. A region of interest 109 is shown within the imaging zone 108. A subject 118, for example a patient, is shown as being supported by a subject support 120, for example a moveable table, such that at least a portion of the subject 118 is within the imaging zone 108 and the region of interest 109.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically, magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 "RF antenna" for manipulating the orientations of magnetic spins within the imaging zone 108 and for receiving radio transmissions from spins also within the imaging zone 108. The radio frequency antenna contains one or multiple coil elements. The radio-frequency coil 114 is connected to an RF amplifier 116. The radio frequency amplifier 116 is providing RF power to the RF coil 114 for manipulating the orientations of magnetic spins within the imaging zone 108.

The amplifier 116 and the gradient controller 112 are shown as being connected to a hardware interface 128 of a computer system 126. Thus, the computer system 126 serves also as receiver for receiving and processing the MR signals acquired using the coil 114.

The computer system further comprises a processor 130 that is in communication with the hardware system 128, a memory 134, and a user interface 132. The memory 134 may be any combination of memory which is accessible to the processor 130. This may include such things as main memory, cached memory, and also non-volatile memory such as flash RAM, hard drives, or other storage devices. In some examples the memory 130 may be considered to be a non-transitory computer-readable medium.

The computer memory 134 is shown as containing machine-executable instructions 140. The machine-executable instructions contain commands or instructions which enable the processor 130 to control the operation and function of the magnetic resonance imaging system 100. The computer memory 134 is shown as further containing imaging scan protocols 142. Each imaging scan protocol may comprise pulse sequence commands for one or multiple pulse sequences which are either instructions or data which may be converted into instructions which enable the processor 130 to control the magnetic resonance imaging system 100 to acquire magnetic resonance data. The pulse sequence commands may therefore be part of an imaging scan protocol. The magnetic resonance data may for instance be used to cause the magnetic resonance imaging system to perform multiple pulse repetitions which cause magnetic resonance signals 144 to be acquired. Each pulse corresponds to the supplying of RF power to the coil 114 by the RF amplifier 116.

Magnetic resonance signals 144 are shown as being stored in the computer memory 134. The magnetic resonance signals 144 for a particular pulse repetition may be collated into the magnetic resonance data 146. The magnetic resonance data 146 may be used to generate a series of images 148. The imaging scan protocols may further comprise instructions 150 regarding the reconstruction of the image data 148 from the MR data 146 acquired using the imaging.

The computer memory 134 is shown as further containing machine-executable instructions as a module 152 which enables the processor 130 to provide a prediction of metastases in image data using a machine learning model 154. Without any restriction to generality in the following it is assumed that the image data used to provide the prediction of metastases is MR image data, like for example data of the images 148.

The module 152 may also be described as an artificial intelligence (AI) component 152. The AI component 152 may be configured for a robust and fast detecting of metastases. The AI component 152 may be configured to perform machine learning on training sets in order to generate one or more machine learning models for predicting metastases in image data. The training process will be described below.

Even though in the above example the module 152 is shown as being part of the computer system 126 used to acquire the MR image data, it is also possible that the module is part of a computer system that is independent of the system 126. A corresponding example is depicted in FIG. 2.

Figure 2:
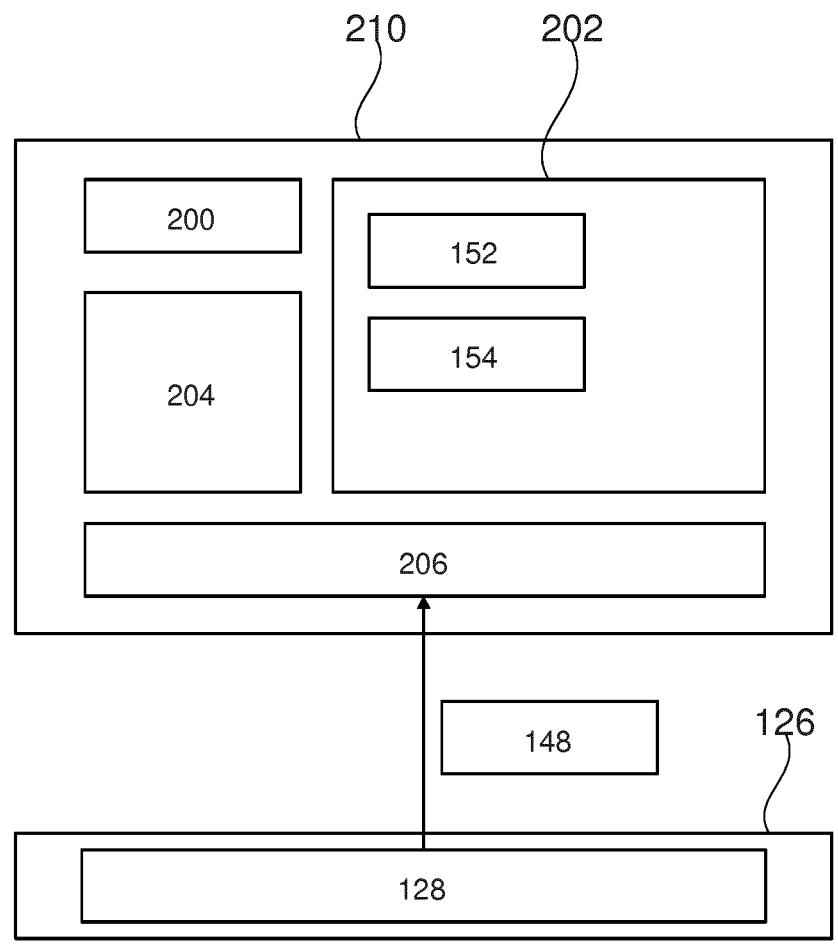
FIG. 2 illustrates an example of a medical analysis system.

FIG. 2 depicts a computer system 210 comprising a processor 200, a memory 202, a hardware interface 206 and a user interface 204. The computer system 210 is a medical analysis system. The medical analysis system 210 may be part of the MRI system 100 of FIG. 1. The hardware interface may for example be a network interface. The memory 202 may be any combination of memory which is accessible to the processor 130. This may include such things as main memory, cached memory, and also non-volatile memory such as flash RAM, hard drives, or other storage devices. Again, in some examples the memory 202 may be considered to be a non-transitory computer-readable medium.

The computer memory 202 is shown as containing machine-executable instructions like for example the module 152. Another example of the instructions is a machine learning model 154. The system 210 may receive image data like the MR image data 148 from the system 126 via the interfaces 128 and 206 that may be communicating with each other over a network like the internet. The module 152 is configured for predicting metastases in a test tissue sample by making use of the machine learning model 154.

This may permit to apply machine learning for intra-organ prediction of metastasis locations. After detection of a primary tumor, the target organs, which are most likely affected by metastases, may be imaged with one or more suitable imaging modalities providing sufficient radiologic information. The resulting images may then enter a suitably trained machine learning algorithm (module 154), which yields information on the probability of metastases locations.

Received via the user interface 204 is for example a description of a tumor of a subject, for example a person. The image data 148 is of a test tissue sample of an anatomy region of that person. The test tissue sample is free of metastases. By inputting the image data and the tumor description to the input of the machine learning model 154, the model 154 can output a prediction of occurrence of metastases originating from the tumor in the test tissue sample. The prediction is then provided to the user interface 204. All this is controlled by the instructions 152.

Figure 3:
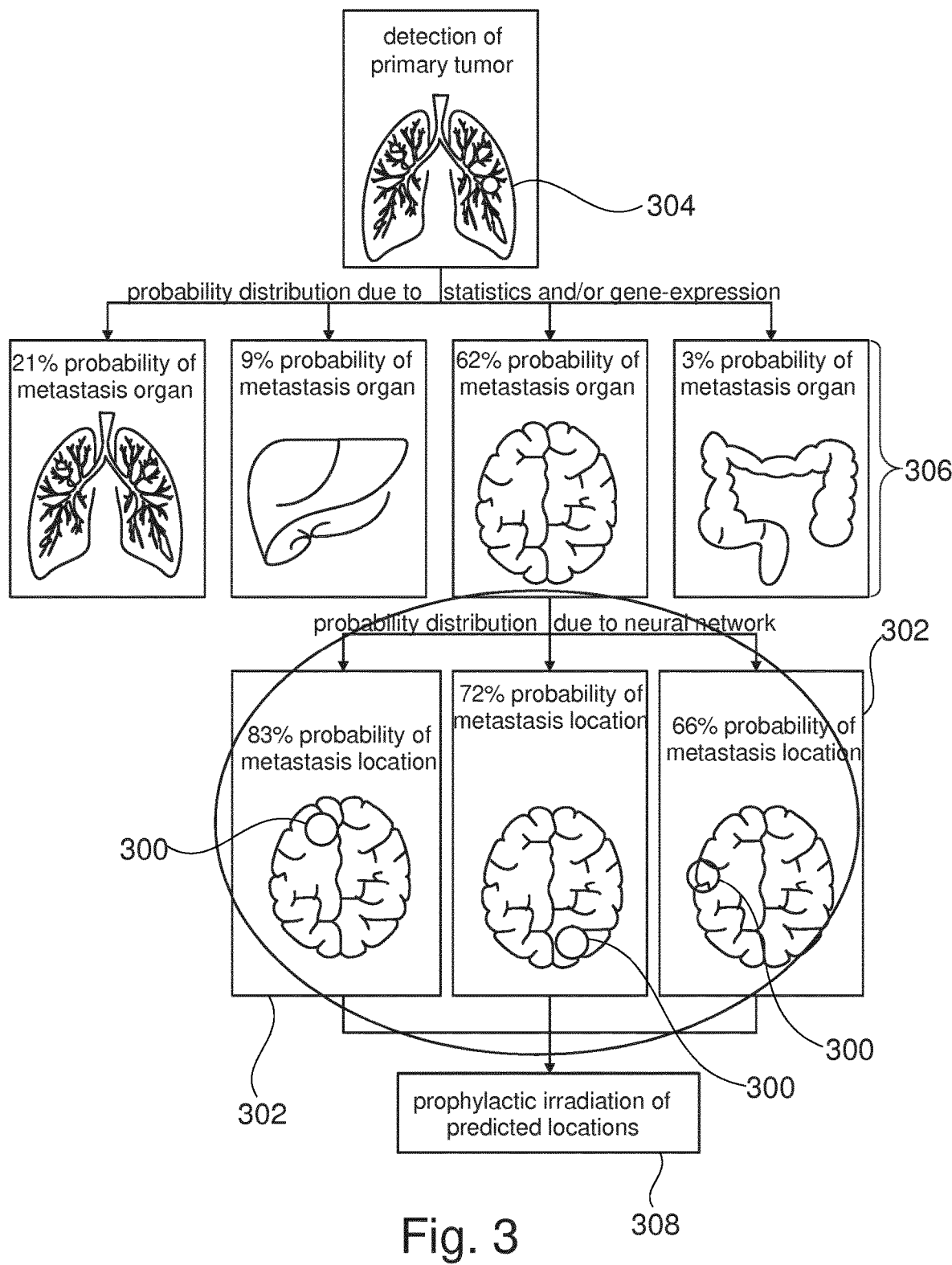
FIG. 3 is a diagram illustrating the relationship between tumor and metastases.

In a practical example, as depicted schematically in FIG. 3, a primary tumor 304 may be detected using any suitable means. Here, the tumor 304 is a lung tumor. Over a certain time period the tumor may cause the development of metastases in certain organs or anatomy regions, like the lung itself, the liver, the brain or the colon of the person. Examples of these regions of anatomy are depicted by reference numeral 306. Assuming the machine learning model was trained for the brain, the input of the tumor description and one or more images 148 of the still healthy anatomy region 'brain' enables the machine learning model 154 to predict the location 300 and probability of future metastases development. A respective prediction image 302 may be provided on the user interface 204.

The locations or regions 300 for which a highly probable development of metastases are predicted, may be subject to a respective prophylactic irradiation treatment (reference numeral 308).

Figure 4:
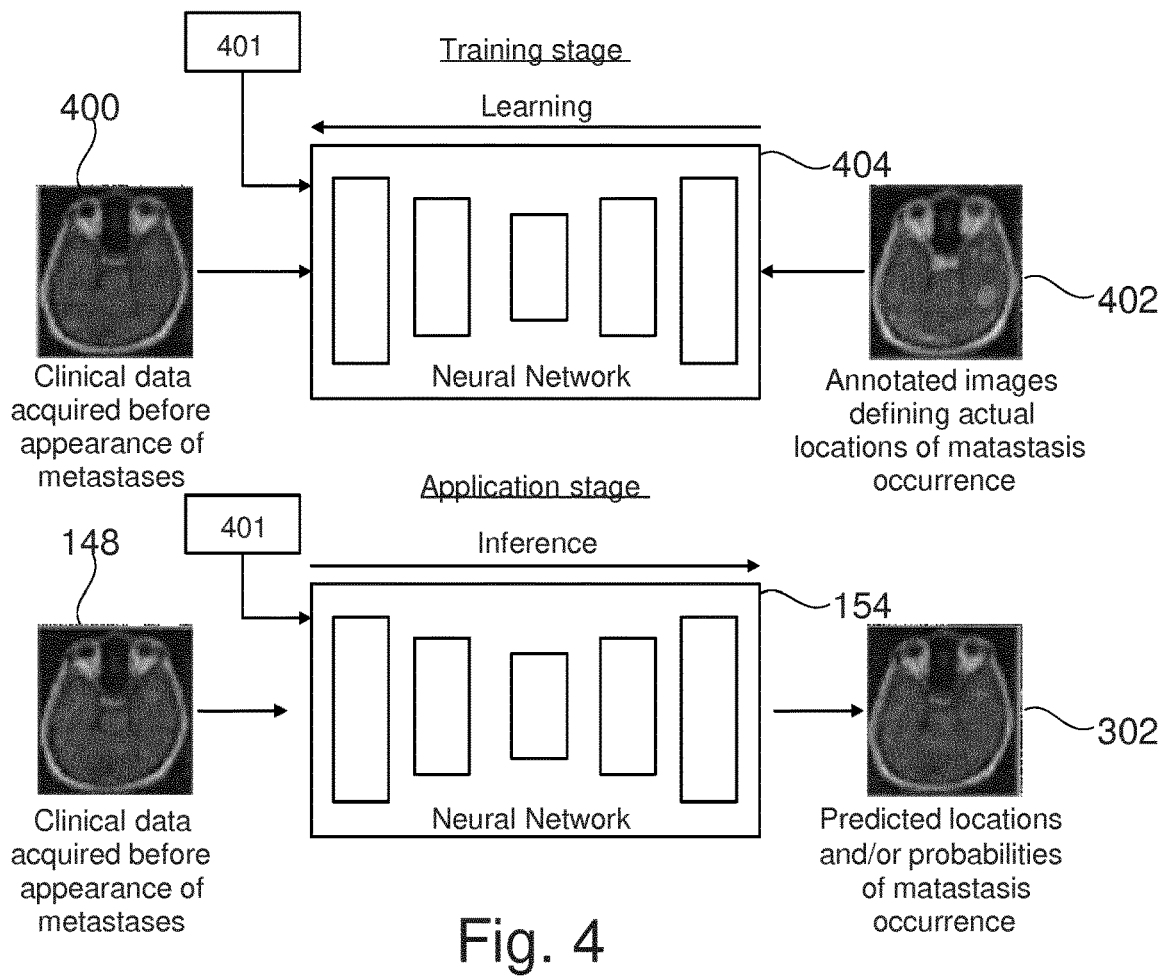
FIG. 4 is a block diagram illustrating the development and usage of a machine learning model.
Figure 5:
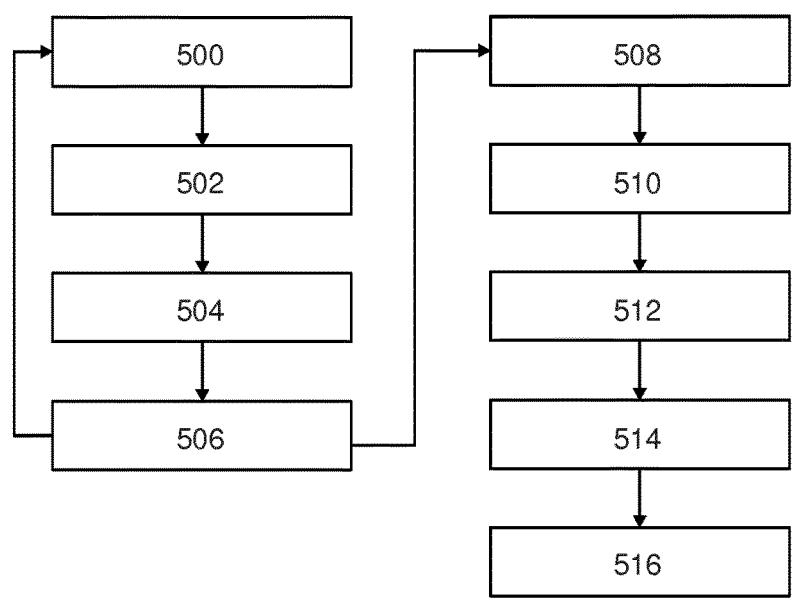
FIG. 5 is a flow chart of training and using a machine learning model.

FIG. 4 is a block diagram showing various steps for obtaining and using the machine learning model 154. The flow chart in FIG. 5 shows corresponding method steps, wherein the left side of blocks 500-506 reflect the training stage and the right side with blocks 508-516 reflect the application or prediction stage.

The method starts in block 500 with the reception of training sets for multiple different ones of training tissue samples of the anatomy region. For example, for different persons that have a tumor, different training sets are received. The tumors may or may not vary between the persons with respect to tumor type and location. However, for an efficient training a large multitude of training sets should be received for a given tumor type and location.

Each received training set is comprising for a respective training tissue sample of an anatomy region image data 400 and image data 402. The image data 400 is free of any metastases and shows a certain anatomy region, whereas the image data 402 was acquired at a later time point and shows metastases of said anatomy region. Said metastases originate from the tumor 304 of the person. For a certain anatomy region, image data 400 and 402 may be provided with different contrasts and/or acquired with different image acquisition techniques as different training sets. Further, each training set further comprises a description 401 of the tumor in the person from which the training tissue sample originates. The description may for example comprise a location description of the tumor 'right lower part of the lung'. In another example the description may alternatively or additionally comprise image data of the region where the tumor is located.

In optional block 502 the image data 402 may be analyzed for the presence of metastases and the location of the metastases may be marked in the image data 402 accordingly. This may be performed by conventional means, like for example neural networks or in general other machine learning models different than the model 154 in an automated manner. Manual marking is also possible.

Optional block 504 is for transforming for all training sets the image data 400 and 402 into a common reference image frame of the anatomy region. This will ensure that any training and later preferably any application is always performed on the same image voxels since different training images 400 and 402 as well as different images 148 may be acquired under different view angels showing differently image sections of the anatomy region.

Finally, in block 506 a learning algorithm 404 is executed on the images 400 and 402, was well as the descriptions 401. This results in a generation of the machine learning model 154.

It has to be noted that any of steps 500-506 described above may be performed on the system 210 using the instructions 152. Steps 500-506 may be repeated multiple times with different training sets—the more training sets are available the more accurate the machine learning model will be.

After the generation of the machine learning model 154, the method continues in block 508 with the provision of the machine learning model 154. In block 510 a tumor description 401 and the image data 148 of (still) metastases free tissue is received. Here, it is assumed that the tumor description 401 describes the type and position of the tumor 304 for which the machine learning model 154 was obtained such that the model is able to make certain predictions regarding said tumor 304.

Again, optional block 512 is for transforming of the image data 148 into the common reference image frame of the anatomy region. In block 514, the description 401 and the (optionally transformed) image data 148 are then input to the machine learning model 154. In block 516 the machine learning model outputs predicted locations and/or probabilities of future metastases occurrence. This may be in form of for example the image 302 that may then be provided to the user interface 204 (FIG. 2).

Thus, for each type of primary tumor investigated, a network is trained with images 400 of the most likely target organs, acquired after appearance of primary tumor but before appearance of metastases. The network is for example a convolutional neural network, such that the learning algorithm is a deep learning algorithm that is based on a convolutional neural network architecture.

For training, images 402 are annotated to the further course of cancer, particularly the exact location (and extent) of the metastases inside the imaged target organs. Thus, in the diagnostic phase, after appearance of primary tumor, images 400 and 402 of the most likely target organs are acquired and fed into the network.

The information subsequently delivered by the trained network in the application stage can have different levels of detail:

the general probability if the target organ will be affected at all or not (i.e., yes/no decision without localization).

a finite number N>1 of discrete locations (i.e., xn/yn/zn-coordinate, 1 . . . n . . . N) with the N highest probabilities of metastasis occurrence within the target organ.

A probability map across the target organ (anatomy region), discretized on a grid with certain voxel size. The discrete locations described in the previous item would appear as local maxima in this probability map.

The images acquired during training and diagnostic phase can be from a single or multiple imaging modalities, e.g. magnetic resonance (MR), computed tomography (CT), ultrasound (US), or positron emission tomography (PET). Furthermore, it can be advantageous to acquire with each modality multiple images with different contrasts, e.g., MR images with T1/T2/diffusion-weighting, pre- and post-contrast injection, etc. A suitable trade-off between imaging effort and predictive power has of course to be found. Furthermore, the approach is not limited to imaging data only, but could incorporate information such as age, gender, lab values, or the patient history as input to the learning algorithm 404 and to the machine learning model 154.

Even though a broad range of machine learning algorithms could be employed for the intra-organ prediction of metastases, deep learning techniques may be considered as the preferred embodiment. Deep learning offers a unified solution for the three different use-cases outlined above. In order to predict the probability for metastases in the presence of a primary tumor, Convolutional Neural Networks (CNNs) may be employed. A CNN consists of a sequence of interconnected layers (i.e. convolutional layer, max-pooling layer, . . . ) resembling the feature extraction step in a classical image processing pipeline, followed by one or more fully connected layers. CNNs are usually trained to predict class labels or probabilities for natural images, or to provide diagnosis for medical images, but the underlying concept can be transferred to describe the field of metastases prediction by a skilled person.

Even though CNNs have been originally developed primarily for the processing of image data, it should be noted that the above mentioned non-image data (tumor description, medical history data) could be easily integrated e.g. in terms of additional input connections at the level of the fully connected layers.

For the prediction of metastases location (including their probabilities), region proposal networks may be considered. Here, in contrast to conventional CNNs, the output neurons no longer correspond to discrete class labels but to voxel locations and metastases probabilities. For this purpose, it may be beneficial if the images of the target organ (region of anatomy) are transformed in a normalized reference frame.

Finally, deep learning-based techniques may also be employed for the generation of probability maps. Given images of the primary tumor, in combination with annotated metastases region in the target organs, the probability at voxel level could be estimated using a patch-wise analysis of a corresponding CNN (centered at the voxel of interest). Alternatively, more efficient networks structures from the field of semantic image segmentation could be employed.

The invention can be extended not only to predict the locations of the metastases, but also time point of metastasis appearance. In case training sets have multiple images 402 showing the time development of metastases, this information could be output with the prediction images 302. In the example of FIG. 3, an output may indicate that the left prediction image 302 has the 83% probability of metastasis 300 at the indicated location within the next 2 months, the middle prediction image 302 has the 72% probability of metastasis 300 at the indicated location within the next 4 months and the right prediction image 302 has the 66% probability of metastasis 300 at the indicated location within the next 6 months.

It has to be noted that the above described principles may be applied where (a) a localized lesion is expected in a certain area, (b) the exact location of the expected lesion is not known a priori, (c) the knowledge of the exact location of the expected lesion offers therapeutic and/or diagnostic advantages. All three conditions are fulfilled by metastases expected from a primary tumor.

LIST OF REFERENCE NUMERALS 100 magnetic resonance imaging system
104 magnet
106 bore of magnet
108 imaging zone
109 region of interest
110 magnetic field gradient coils
112 magnetic field gradient coil power supply
114 radio-frequency coil
116 RF amplifier
118 subject
120 subject support
126 computer system
128 hardware interface
130 processor
132 user interface
134 computer memory
140 machine-executable instructions
142 pulse sequence commands
144 magnetic resonance signals
146 magnetic resonance data
148 magnetic resonance images
150 image reconstruction instructions
152 instructions for metastasis prediction
154 machine learning model
200 processor
202 memory
204 user interface
206 hardware interface
210 medical analysis system
300 metastasis
302 prediction image
304 primary tumor
306 region of anatomy
308 treatment
400 image
401 tumor information
402 image
404 machine learning algorithm
500-506 training stage
508-516 application stage

The invention claimed is:

1. A computer implemented medical analysis method for predicting metastases in a test tissue sample, the method comprising:
   providing a trained first machine learning model having an input and an output,
   receiving a description of a tumor and first image data of a test tissue sample of an anatomy region, separate from the tumor and the test tissue sample being free of metastases, wherein the description of the tumor includes one or more of a spatial location of the tumor with respect to the anatomy of the subject carrying the tumor, a classification of the tumor, image data of the tumor,
   providing the first image data and the tumor description to the input of the first machine learning model,
   in response to the providing, receiving from the output of the first machine learning model a prediction of occurrence of metastases originating from the tumor in the test tissue sample, and
   providing the prediction.

2. The method of claim 1, further comprising
   receiving training sets for multiple different ones of training tissue samples of the anatomy region, each training set comprising for a respective one of the training tissue samples second image data and third image data, the third image data being data acquired after occurrence of a metastasis in the subject from which the training tissue sample originates, the second image data (representing the training tissue sample free of metastases, wherein each training set further comprises a description of the tumor in the subject from which the training tissue sample originates,
   executing a learning algorithm on the training sets for generating the first machine learning model.

3. The method of claim 2, wherein the second image data and the third image data represent a 3D volume of the anatomy.

4. The method of claim 2, the third image data being a set of time-resolved image data, wherein the indications are time-resolved.

5. The method of claim 2, further comprising analyzing the third image data for the presence of metastases in the respective training tissue sample, and annotating the third image data regarding the results of the analysis.

6. The method of claim 1, the prediction of occurrence of metastases comprising anyone of:
   an indication if the test tissue sample will be affected by metastases originating from the tumor,
   a probability map across the anatomy region having indications at which discrete locations of the anatomy region will be affected by metastases originating from the tumor.

7. The method of claim 6, the indication comprising anyone of:

a probability value, the probability value describing the probability at which the metastases have to be expected, a binary value, the binary value describing if metastases have to be expected or not.

8. The method of claim 1, the first image data, the second image data, the third image data and the image data of the tumor being anyone of: magnetic resonance image data, computed tomography image data, ultrasound image data, positron emission tomography image data, X-Ray data.

9. The method of claim 1, further comprising receiving medical history data of the subject carrying the tumor and providing the medical history data to the input of the machine learning model, the training set further comprising medical history data of the subject carrying the tumor.

10. The method of claim 1, the learning algorithm being a deep learning algorithm.

11. The method of claim 10, the deep learning algorithm being based on a convolutional neural network architecture, the method further comprising:

transforming for all training sets the second image data and the third image data into a common reference image frame of the anatomy region, performing the execution of the learning algorithm on the training sets comprising the transformed image data for generating the first machine learning model.

12. A computer program product comprising machine executable instructions for execution by a processor, wherein execution of the machine executable instructions causes the processor to execute the method of claim 1.

13. A medical analysis system for predicting metastases in a test tissue sample, the system comprising a memory containing machine executable instructions and a processor for controlling the medical analysis system, wherein execution of the machine executable instructions causes the processor to:

providing a trained first machine learning model having an input and an output, receiving a description of a tumor and first image data of a test tissue sample of an anatomy region, separate from the tumor and the test tissue sample being free of metastases, wherein the description of the tumor includes one or more of a spatial location of the tumor with respect to the anatomy of the subject carrying the tumor, a classification of the tumor, image data of the tumor, providing the first image data and the tumor description to the input of the first machine learning model, in response to the providing, receiving from the output of the first machine learning model a prediction of occurrence of metastases originating from the tumor in the test tissue sample, and providing the prediction.

14. An MRI system comprising the medical analysis system of claim 13, the MRI system being configured for acquiring the first image data.

* * * * *